(12) United States Patent
Vaillant et al.

(10) Patent No.: US 10,163,211 B2
(45) Date of Patent: Dec. 25, 2018

(54) SYSTEM AND METHOD FOR ENHANCED VISUALIZATION OF MULTIPLE LOW CONTRAST OBJECTS WITHIN AN IMAGED SUBJECT

(71) Applicant: General Electric Company, Schenectady, NY (US)

(72) Inventors: Regis Vaillant, Villebon sur Yvette (FR); Maxime Cazalas, Paris (FR); Liliane Ramus, Verailles (FR); Sophie Amelot, Marly-le-Roi (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 142 days.

(21) Appl. No.: 15/006,600

(22) Filed: Jan. 26, 2016

(65) Prior Publication Data

US 2017/0213343 A1 Jul. 27, 2017

(51) Int. Cl.
| | |
|---|---|
| *G06T 7/33* | (2017.01) |
| *G06T 7/00* | (2017.01) |
| *G06T 11/60* | (2006.01) |
| *A61B 6/00* | (2006.01) |
| *G06T 5/50* | (2006.01) |

(52) U.S. Cl.
CPC .............. *G06T 7/0028* (2013.01); *A61B 6/50* (2013.01); *G06T 5/50* (2013.01); *G06T 7/0012* (2013.01); *G06T 7/33* (2017.01); *G06T 11/60* (2013.01); *G06T 2207/10004* (2013.01); *G06T 2207/10121* (2013.01); *G06T 2207/20221* (2013.01); *G06T 2207/30021* (2013.01); *G06T 2207/30101* (2013.01); *G06T 2207/30204* (2013.01)

(58) Field of Classification Search
CPC . A61B 6/50; G06T 11/60; G06T 2207/10004; G06T 2207/10121; G06T 2207/20221; G06T 2207/30021; G06T 2207/30101; G06T 2207/30204; G06T 5/50; G06T 7/0012; G06T 7/0028; G06T 7/33
USPC ........................................................ 382/128
See application file for complete search history.

(56) References Cited

U.S. PATENT DOCUMENTS

| | | | |
|---|---|---|---|
| 6,532,380 B1 | 3/2003 | Close et al. | |
| 7,734,328 B2 * | 6/2010 | Vaillant | G06T 7/00 382/131 |
| 8,515,146 B2 * | 8/2013 | Zhu | G06T 5/006 382/128 |

(Continued)

OTHER PUBLICATIONS

Sotiras, A. et al., "Deformable Medical Image Registration: A Survey," IEEE Transactions on Medical Imaging, vol. 32, Issue 7, pp. 1153-1190, (Jul. 2013).

(Continued)

*Primary Examiner* — Manuchehr Rahmjoo

(57) ABSTRACT

A method for enhancing the visualization of a plurality of objects within an imaged subject. The method includes acquiring a plurality of images of the plurality of objects disposed in the imaged subject and supported by a plurality of guide wires; generating a complex deformation field based at least in part on a plurality of landmarks disposed in the plurality of images; and generating a composite image based at least in part on the complex deformation field. The complex deformation field models deformation induced on the plurality of objects by at least two or more guide wires of the plurality.

18 Claims, 8 Drawing Sheets

(56) References Cited

U.S. PATENT DOCUMENTS

| | | |
|---|---|---|
| 8,989,461 B2 | 3/2015 | Zhu et al. |
| 2005/0074158 A1 | 4/2005 | Kaufhold et al. |
| 2005/0080429 A1* | 4/2005 | Freyman ............... A61B 5/061 606/108 |
| 2006/0074485 A1 | 4/2006 | Realyvasquez |
| 2008/0009938 A1 | 1/2008 | Huang et al. |
| 2008/0199097 A1* | 8/2008 | Mory ..................... G06T 5/50 382/254 |
| 2011/0135176 A1 | 6/2011 | Lendl |
| 2016/0338613 A1* | 11/2016 | Beckers .......... G01R 33/56308 |

OTHER PUBLICATIONS

Extended European Search Report and Opinion issued in connection with corresponding EP Application No. 16204701.3 dated Jun. 19, 2017.

Vincent Bismuth et al; "A Comprehensive Study of Stent Visualization Enhancement in X_Ray Images by Image Processing Means"; Medical Images Analysis; Apr. 14, 2011; pp. 1-13; France.

* cited by examiner

SYSTEM AND METHOD FOR ENHANCED VISUALIZATION OF MULTIPLE LOW CONTRAST OBJECTS WITHIN AN IMAGED SUBJECT

BACKGROUND

Technical Field

Embodiments of the invention relate generally to visualizing objects within an imaged subject.

Discussion of Art

Coronary artery disease is the narrowing of coronary arteries via the accumulation/buildup of athermanous plaque on the artery wall. An artery that has a significant amount of plaque buildup is commonly known as a "clogged" artery. If left untreated, the flow of blood through a clogged coronary artery may be impaired such that the heart's muscular tissue becomes damaged to the point where it is no longer able to contract. The failure of the heart to contract, commonly known as a heart-attack, is often fatal.

Presently, one method of treating coronary artery disease is an angioplasty procedure which involves inserting an expanding metal mesh, known as a "stent," within a clogged artery such that the stent expands the circumference of the artery by pressing against the interior wall of the artery. Such stents are typically inserted/deployed within a coronary artery by first placing a collapsed stent over a deflated angioplasty balloon attached to a guide wire. The guide wire, with the attached balloon and collapsed stent, is then inserted into a major artery of a patient's vascular tree that connects to the clogged artery. Next, the guide wire is used to position the stent and balloon at an insertion site within the clogged artery. Once in position, the balloon is inflated, thereby deploying/expanding the stent against the interior wall of the clogged artery. The balloon is then deflated and removed, via the guide wire, from the insertion site.

An angioplasty procedure is typically performed in conjunction with an X-ray fluoroscopy procedure in which a fluoroscopic imaging system provides real time visualizations, hereinafter also referred to as a "live X-ray video feed" or "X-ray video feed," of the guide wire, balloon, stent, and/or other tools, within an imaged subject (e.g., the patient undergoing the angioplasty procedure). Many fluoroscopic imaging systems provide an X-ray video feed having a resolution at or near fifteen frames per second ("fps"). Stents, however, have a low contrast to noise ratio and are often subject to rapid movements due to a patient's cardiac rhythm. The low contrast to noise ratio and rapid movements typically make it difficult to identify a stent and/or accompanying guide wire within any single frame of an X-ray video feed.

Thus, some current fluoroscopic imaging systems use various image processing technologies to improve visualization of a stent and/or guide wire within a patient's vascular tree. For example, some image processing technologies typically include attaching two objects with a high contrast to noise ratio, known as a "markers," to the guide wire in relation to the stent. By identifying the position of the markers, some fluoroscopic imaging systems can identify and/or estimate the position of the stent. Currently, such fluoroscopic imaging systems are only able to accurately improve the visualization of a single stent having two markers. Some types of angioplasty procedures, however, such as those for treating a lesion at a bifurcation, involve the placement of two stents which are typically positioned at an insertion site located at the junction of two coronary arteries.

Accordingly, in such angioplasty procedures, it is often the case that the stents must be deployed so that only two markers are visible within any single frame of the live X-ray feed. For example, the stents may be deployed one at a time with each stent being marked by two markers. However, deploying two stents in such a manner increases the duration of the angioplasty procedures and the risk to the patient. Alternatively, the stents may be simultaneously deployed with only one stent being marked by markers. However, deploying two stents in such a manner increases the risk that the unmarked stent will be incorrectly deployed.

What is needed, therefore, is a system and method that enhances the visualization of multiple stents, and/or other low contrast objects, simultaneously within an imaged subject.

BRIEF DESCRIPTION

In an embodiment, a method for enhancing the visualization of a plurality of objects within an imaged subject is provided. The method includes acquiring a plurality of images of the plurality of objects disposed in the imaged subject and supported by a plurality of guide wires; generating a complex deformation field based at least in part on a plurality of landmarks disposed in the plurality of images; and generating a composite image based at least in part on the complex deformation field. The complex deformation field models deformation induced on the plurality of objects by at least two or more guide wires of the plurality.

In yet another embodiment, an imaging system for enhancing the visualization of two or more objects within an imaged subject is provided. The system includes a controller including at least one processor and a memory device. The memory device stores an imaging application which when loaded into the at least one processor adapts the controller to enhance, via a complex deformation field based at least in part on a plurality of landmarks disposed within a plurality of images acquired by the imaging system, the visibility of the two or more objects in a composite image. The complex deformation field models deformation induced on the two or more objects by two or more guide wires that support the two or more objects.

In yet another embodiment, a method for simultaneously enhancing the visualization two or more stents disposed within a patient is provided. The method includes acquiring a first image and a second image; and applying a complex deformation field to at least one of the first and the second images to generate a frame of a video feed. Both images include the two or more stents, and each stent is supported by a guide wire that includes a pair of markers disposed on opposite sides of the stent. The complex deformation field is based at least in part on two or more weighted deformation fields. Each of the two or more weighted deformation fields is based at least in part on one or more of the pairs of markers of the guide wires supporting the two or more stents.

DRAWINGS

The present invention will be better understood from reading the following description of non-limiting embodiments, with reference to the attached drawings, wherein below:

DETAILED DESCRIPTION

Figure 1:
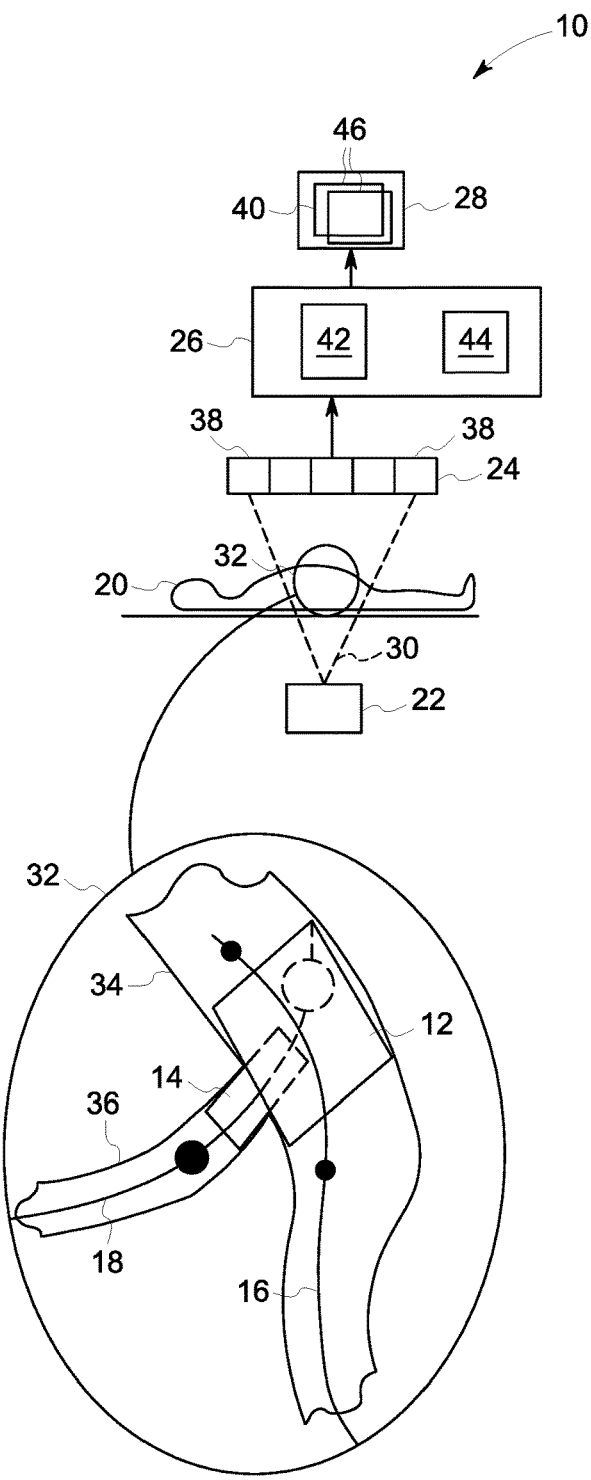
FIG. 1 is a block diagram of an exemplary imaging system that acquires a plurality of images of objects disposed within an imaged subject in accordance with embodiments of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled, "electrically connected" and "electrical communication" means that the referenced elements are directly or indirectly connected such that an electrical current may flow from one to the other. The connection may include a direct conductive connection (i.e., without an intervening capacitive, inductive or active element), an inductive connection, a capacitive connection, and/or any other suitable electrical connection. Intervening components may be present. As also used herein, the term "deformation" describes the change in shape, location, and/or appearance of the locations, positions, and/or appearances of common points between two or more images. Accordingly, the term "deformation field," as used herein, means a model which can be used to depict, describe, and/or otherwise show the deformation between two or more images. For example, in embodiments, a deformation field may be a vector field in which the magnitude and direction of the deformation of one or more common points between a first image and a second image is modeled by vectors, each vector representing the deformation of one of the common points.

Additionally, while the embodiments disclosed herein are described with respect to a fluoroscopic imaging systems, it is to be understood that embodiments of the present invention are equally applicable to devices such as Magnetic Resonance Imaging ("MRI"), real-time endoscopic imaging, an/or any other type of imaging where multiple images are acquired in order to produce a visual representation of one or more objects within an imaged subject. As will be appreciated, embodiments of the present invention related imaging systems may be used to analyze objects within any material which can be internally imaged, generally. As such, embodiments of the present invention are not limited to analyzing objects within human tissue.

Referring to FIG. 1, an imaging system 10 for simultaneously enhancing the visualization of one or more objects 12, 14, 16 and 18, which may be low contrast objects, within an imaged subject 20 is shown. The system 10 includes a radiation source 22, a detector 24, a controller 26, and a display screen 28. The radiation source 22 projects a radiation beam 30 through an area of interest 32 of the imaged subject 20 within which the one or more objects 12, 14, 16 and 18 are disposed. For example, as shown in FIG. 1, the imaged subject 20 may be a patient undergoing an angioplasty procedure, the area of interest 32 may be the junction of two or more coronary arteries 34 and 36, and the objects may be two stents 12 and 14 attached to two guide wires 16 and 18. The radiation beam 30 is received by the detector 24 which generates a plurality of images 38 that are then communicated to the controller 26 which generates a video feed 40 that is transmitted to and displayed by the display screen 28.

The controller 26 includes at least one processor 42 and at least one memory device 44, and is in communication with both the detector 24 and the display screen 28. In embodiments, the controller 26 may be in further communication with the radiation source 22. An imaging program/application may be stored in the at least one memory device 44 that, when loaded into the at least one processor 42, adapts the controller 26 to generate the video feed 40 by processing the images 38 received from the detector 24. In embodiments, the imaging program may further adapt the controller 26 to control the detector 24 and/or the radiation source 22.

The video feed 40 includes a plurality of frames 46. As used herein, the term frame describes a composite image that may be based at least in part on one or more of the plurality of images 38 acquired by the system 10. For instance, in embodiments, a composite image/frame 46 may be generated by registering one or more of the acquired images 38 to a reference image selected from the plurality of images 38. The registration of one or more images 38 to a reference image increases the contrast of at least one or more of the objects 12, 14, 16, 18 within the produced/generated frame 46. Accordingly, in embodiments, each frame 46 may be based at least in part on one or more of the images 38 received by the controller 26 from the detector 24. Once a frame 46 has been generated, it is transmitted, as part of the video feed 40, by the controller 26 to the display screen 28. In other words, in embodiments, the displayed video feed 40 is a processed form of the raw images 38 acquired by the system 10. In embodiments, the video feed 40 may be a live/real time and/or near-real time feed. In other embodiments, one or more of the frames 46 may be still images (e.g., a photograph).

Figure 2:
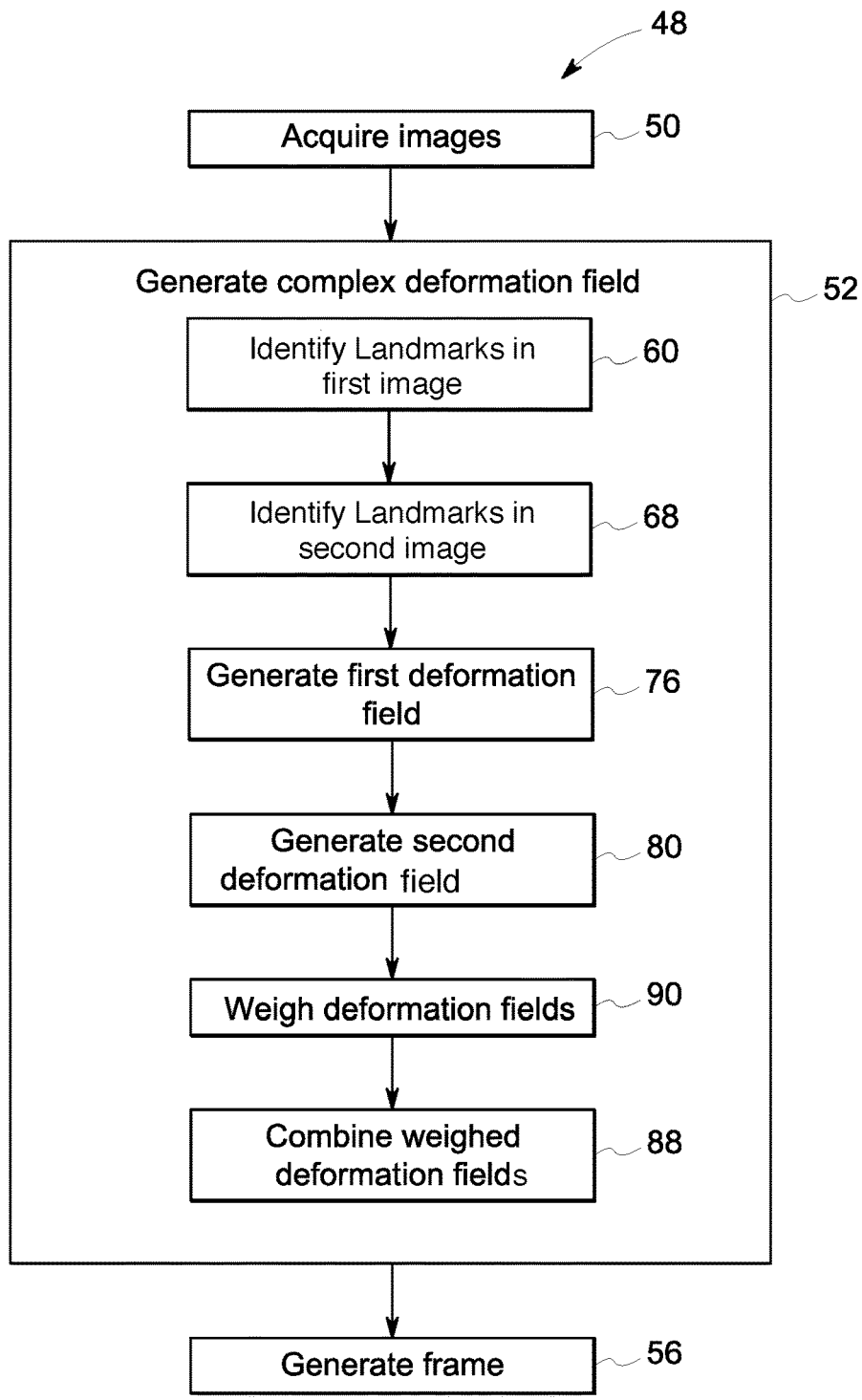
FIG. 2 is a flowchart showing a method that incorporates the imaging system of FIG. 1 to simultaneously enhance the visualization of multiple objects within an imaged subject in accordance with embodiments of the present invention.
Figure 8:
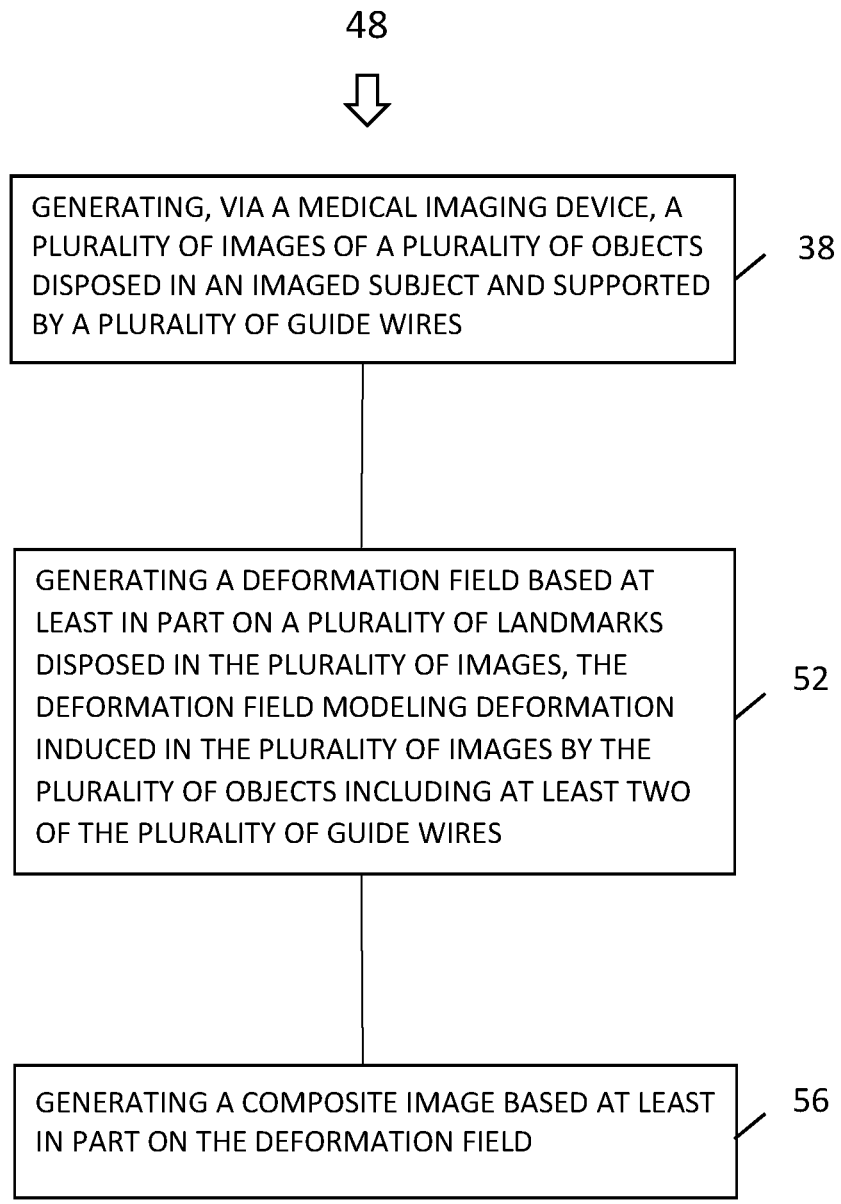
FIG. 8 is a flowchart showing a method that incorporates the imaging system of FIG. 1 to simultaneously enhance the visualization of multiple objects within an imaged subject in accordance with embodiments of the present invention.

Turning now to FIGS. 2 and 8, a method 48 that incorporates the imaging system 10 to enhance the visualization of the multiple objects 12, 14, 16, 18 within the imaged subject 20 is shown. In embodiments, the imaging program/application may adapt the controller 26 to perform the method 48. Accordingly, in embodiments, the method 48 includes: acquiring 50 the plurality of images 38 of the objects 12, 14, 16, 18 disposed within the imaged subject 20; generating 52 a complex deformation field (54 in FIG. 6); and generating 56 a composite image/frame (46 in FIGS. 1 and 58 in FIG. 6) of the video feed 40 based at least in part on the complex deformation field 54.

Figure 6:
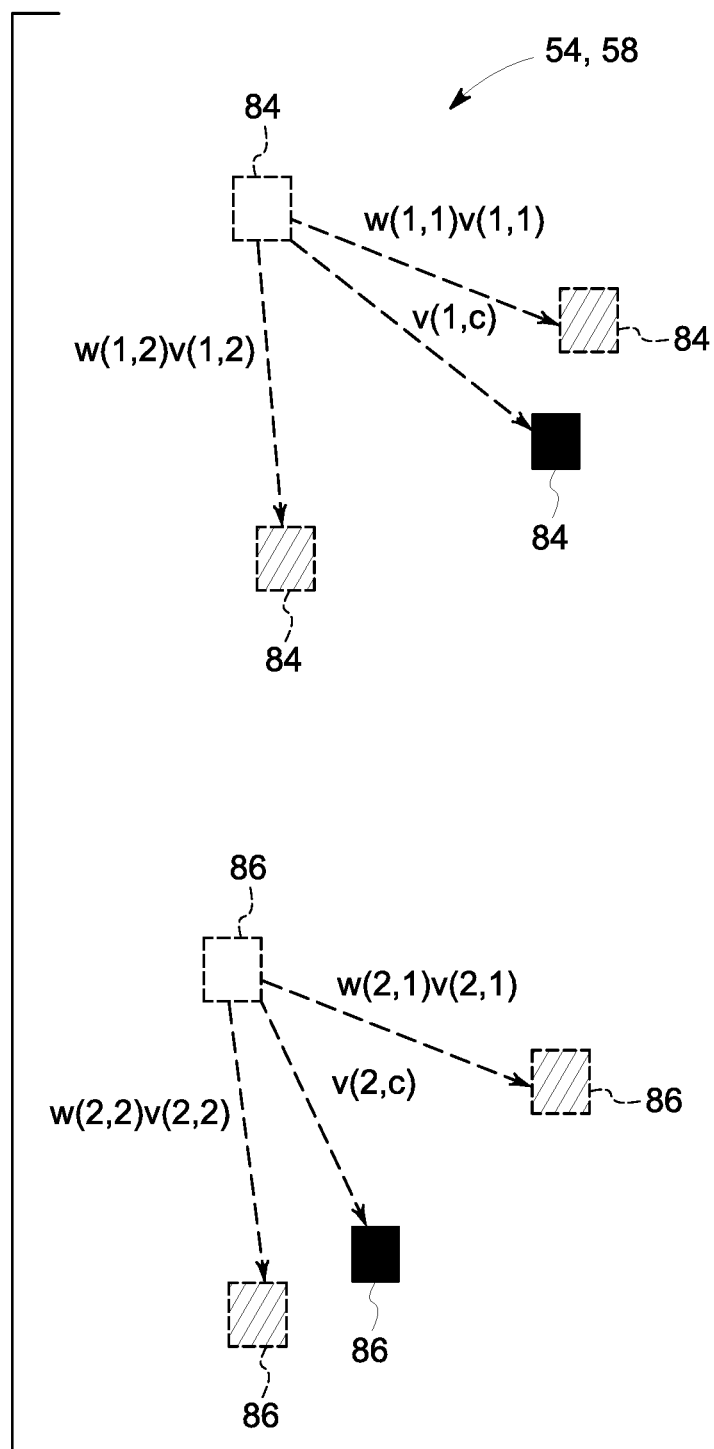
FIG. 6 is a diagram of a frame generated by the system of FIG. 1.

Referring briefly to FIG. 6, in embodiments, the frame 58 depicts at least one of the objects 12, 14, 16, 18 with an enhanced visibility (e.g., at least one of the objects 12, 14, 16, 18 is easier to see in the frame 58 than in some and/or most of the individual acquired images 38). For the purposes of clarity in depicting the complex deformation field 54, however, the objects 12, 14, 16, 18, have not been drawn in FIG. 6. Thus, it is to be understood that in actuality, at least one of the objects 12, 14, 16, 18 is visible/shown in the frame 58.

Returning back to FIG. 2, acquiring 50 the plurality of images 38 of the objects 12, 14, 16, 18 disposed within the imaged subject 20 may be accomplished by known means (e.g., a fluoroscopic imaging system, MRI, PET/MRI, X-RAY, ultrasound, etc.). In embodiments, the images 38 may be acquired in real time and/or near-real time. In other embodiments, the images 38 may be acquired over a longer period of time and/or may be time-exposed images.

Figure 3:
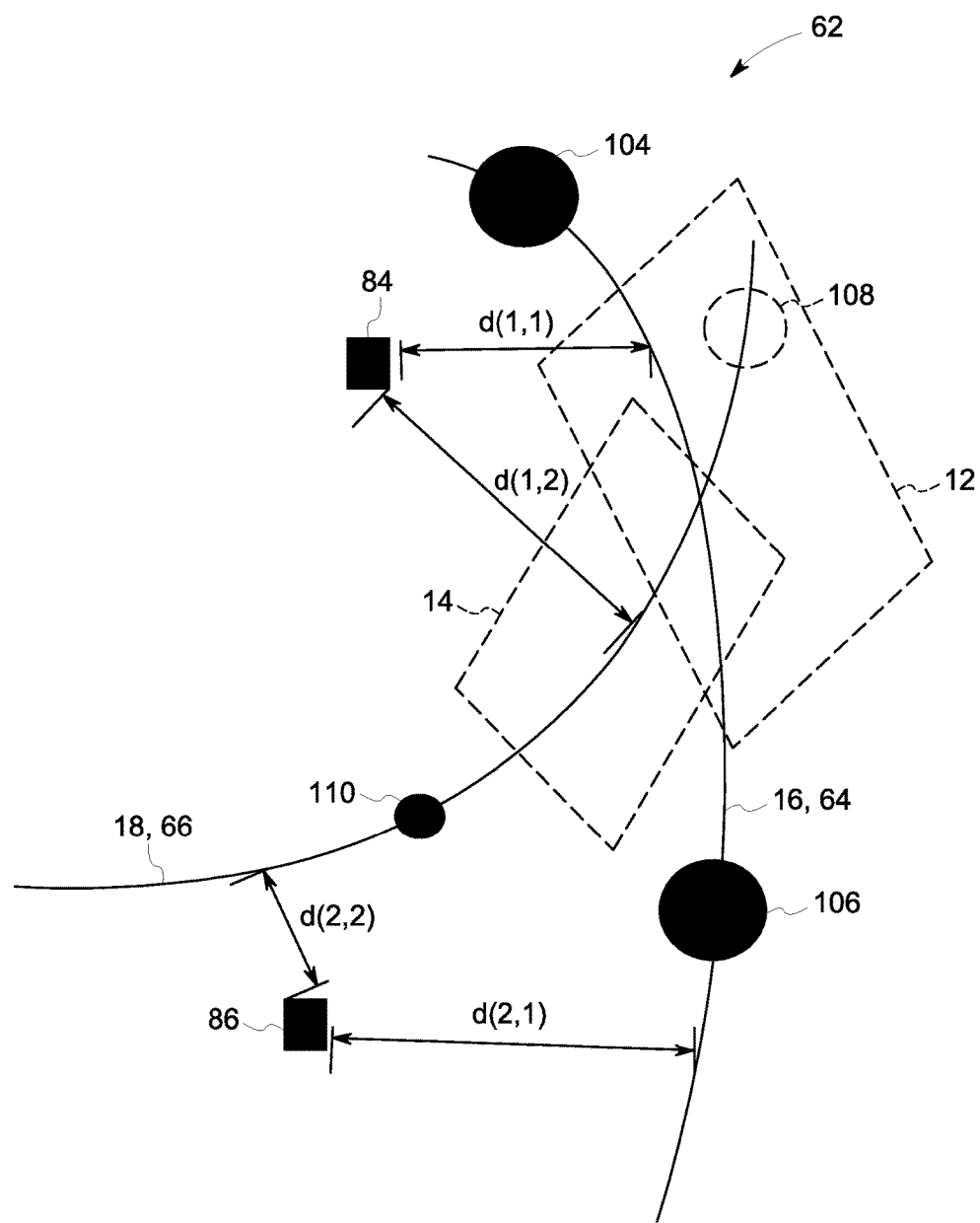
FIG. 3 is a diagram of a first image of the plurality of images acquired by the system of FIG. 1.

As shown in FIGS. 2-3 and 6, the complex deformation field 54 models the deformation induced in the plurality of images 38. In embodiments, the complex deformation field 54 may model the deformation induced by both the first 16 and the second 18 guide wires. As such, the complex deformation field 54 may be based at least in part on a plurality of landmarks which may include the first 16 and the second 18 guide wires. As used herein, the term landmark means an object of which the position of can be readily identified within one of the images 38 acquired by the system 10. For example, landmarks may include guide wires and/or specialized markers. Such markers may or may not be attached to one or more guide wires. By detecting the change in position of one or more landmarks from one image 38 of the plurality to the next, the controller 26 can determine the deformation induced by the guide wires 16 and 18 on the objects 12, 14, 16, 18 and/or other items within the one or more images 38.

Accordingly, generating 52 the complex deformation field 54 may include identifying 60, in a first image 62 of the plurality of images 38, a first position 64 of a first landmark/guide-wire 16, and a first position 66 of a second landmark/guide-wire 18. In embodiments, the detected/identified first positions 64 and 66 of the first 16 and the second 18 landmarks/guide wires serve as a base reference with respect to the positions of the first 16 and the second 18 landmarks/guide wires in another image that will be combined with the first image 62 to generate a frame of the plurality 58.

Figure 4:
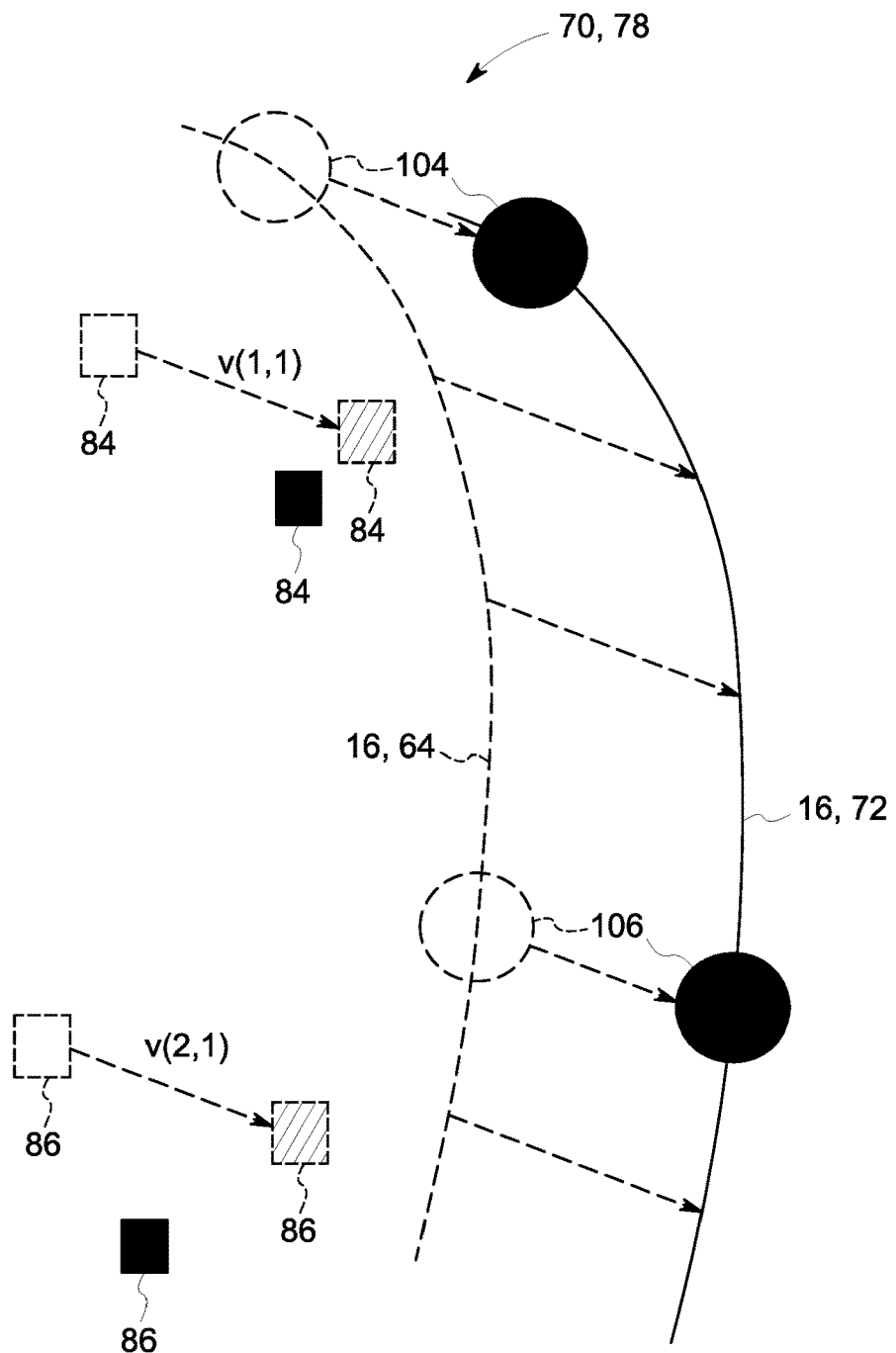
FIG. 4 is a diagram of a second image of the plurality of images acquired by the system of FIG. 1.
Figure 5:
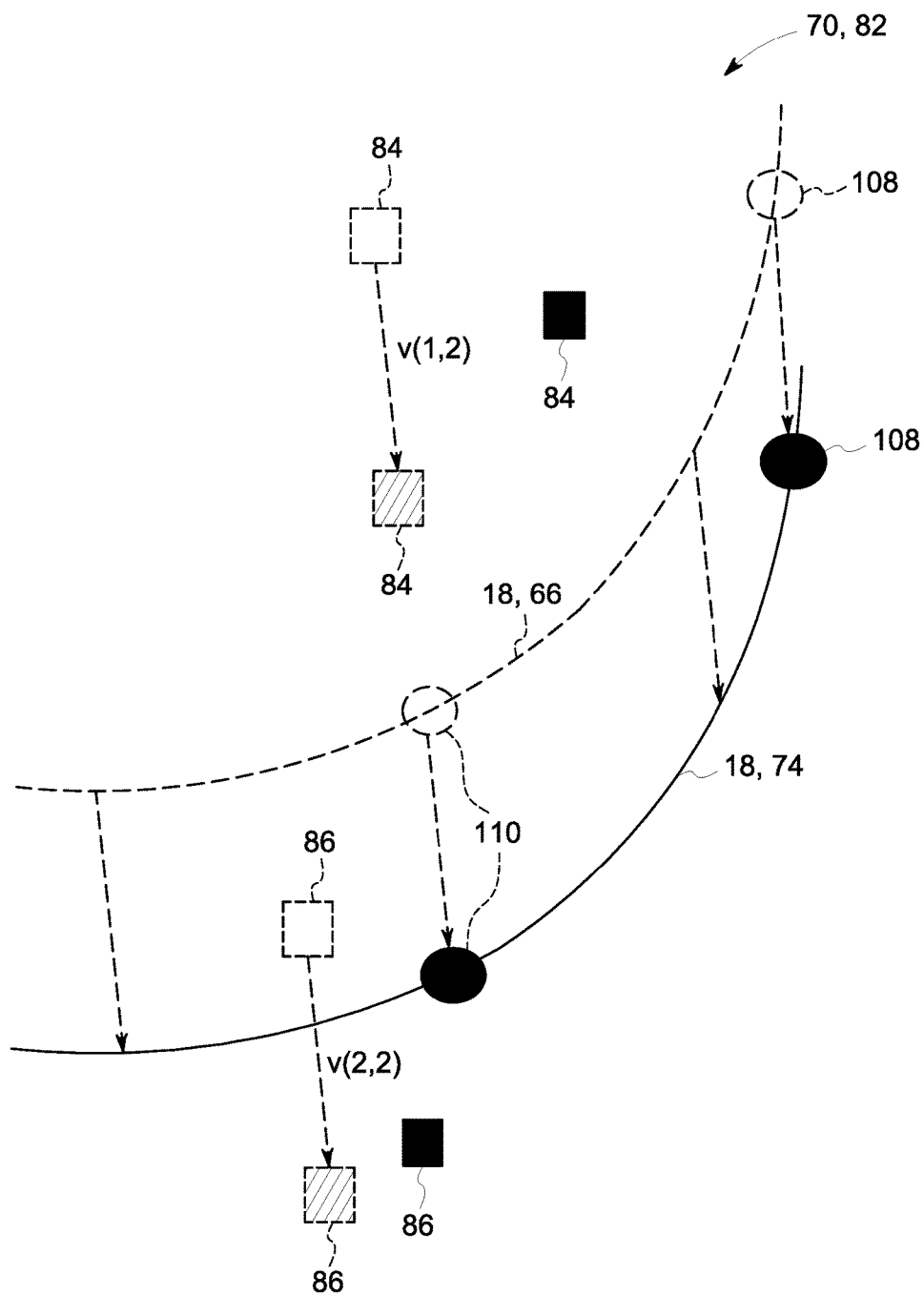
FIG. 5 is another diagram of the second image of the plurality of images acquired by the system of FIG. 1.

Accordingly, as can be seen in FIGS. 2, 4, and 5, generating 52 the complex deformation field 54 may further include identifying 68, in a second image 70 of the plurality of images 38, a second position 72 of the first landmark/guide-wire 16, and a second position 74 of the second landmark/guide-wire 18. In such embodiments, generating 52 the complex deformation field 54 may be based at least in part on the first 64, 66 and the second 72, 74 positions of both the first 16 and the second 18 landmarks/guide wires. For example, by comparing the difference in positions of the first 16 and the second 18 landmarks/guide wires between the first 62 and the second 70 images, the controller 26 can determine/model the deformation induced by the first 16 and the second 18 guide wires between the first 62 and the second 70 images.

As is to be appreciated, while FIG. 3 shows the first positions 64, 66 of the first 16 and the second 18 landmarks/guide wires simultaneously in the first image 62, the second positions 72 and 74 of the first 16 and the second 18 landmarks/guide wires, however, are shown independently of each other in the second image 70 in FIGS. 4 and 5, respectively, for the purpose of clarity. Thus, it is to be understood that in embodiments, the second image 70 simultaneously shows both the second positions 72 and 74 of the first 16 and the second 18 landmarks/guide wires. Additionally, the first positions 64 and 66 of the first 16 and the second 18 landmarks/guide wires have been stenciled into FIGS. 4 and 5, respectively, to better illustrate the movement of the first 16 and the second 18 landmarks/guide wires between the first 62 and the second 70 images.

Referring now to FIGS. 2 and 4-6, generating 52 the complex deformation field 54 may further include generating 76 a first deformation field (78 in FIG. 4) and generating 80 a second deformation field (82 in FIG. 5). The first 78 and the second 82 deformation fields may be based at least in part on the first 64, 66 and the second 72, 74 positions of the first 16 and the second 18 landmarks/guide wires, respectively.

Accordingly, as shown in FIGS. 3-6, the first 78 and the second 82 deformation fields may have one or more points 84, 86 common between the first 78 and the second 82 deformation fields and which may appear in the first 62 and the second 70 images as well as in the generated frame 58. In such embodiments, the points 84 and 86 may represent locations within the first 62 and the second 70 images (e.g. pixels and/or voxels). As is to be appreciated, the points 84 and 86 have been stenciled into FIGS. 4-6 for the purposes of demonstrating the impact of deformation induced by the first 16 and/or the second 18 landmarks/guide wires. Thus, in embodiments, only the solid black squares 84 and 86 are visible in the first image 62, the second image 70, and/or the generated frame 58.

For example, in FIG. 3, the solid black squares 84 and 86 represent the actual positions of the common points 84 and 86 in the first image 62. In FIGS. 4 and 5, the solid black squares 84 and 86 represent the actual positions of the common points 84 and 86 in the second image 70, the clear squares 84 and 86 represent the positions from which the common points 84 and 86 have been deformed away from (i.e., the previous actual positions of common points 84 and 86 in the first image 62), and the shaded squares 84 and 86 represent estimated position of the common points 84 and 86 due to the impact of the deformation induced by the first 16 and the second 18 guide wires between the first 62 and the second 70 images, respectively. In other words, the shaded squares in FIG. 4 are the estimated positions of the common points 84 and 86 due to the impact of the deformation induced by the first guide wire 16. Similarly, the shaded squares in FIG. 5 are the estimated positions of the common points 84 and 86 due to the impact of the deformation induced by the second guide wire 18.

In FIG. 6, the clear squares 84 and 86 again represent the positions from which the common points 84 and 86 have been deformed away from (i.e., the previous actual positions of common points 84 and 86 in the first image 62), the shaded squares 84 and 86 represent the estimated positions of the common points 84 and 86 due to the impact of the deformation induced by the first 16 and/or the second 18 guide wires between the first 62 and the second 70 images, and the solid black squares 84 and 86 represent the depicted positions of the common points 84 and 86 in the generated frame 58.

As shown in FIG. 3, point 84 may be located from the first 16 and the second 18 landmarks/guide wires at distances $d(1,1)$ and $d(1,2)$, respectively, in the first image 62. Similarly, point 86 may be located from the first 16 and the second 18 landmarks/guide wires at distances of $d(2,1)$ and $d(2,2)$, respectively, in the first image 62.

Turning now to FIGS. 4 and 5, the deformation induced by the first 16 and the second 18 guide wires between the first 62 and the second 70 images may be modeled/calculated at each of the one or more points 84 and 86 (e.g., pixels/voxels) common between the first 62 and second 70 images. For example, a shown in FIG. 4, the deformation induced by the first guide wire 16 on the first 84 and the second 86 points between the first 62 and the second 70 images may be modeled by the first deformation field 78 as shown by vectors v(1,1) and v(2,1), respectively. Similarly, as shown in FIG. 5, the deformation induced by the second guide wire 18 on the first 84 and the second 86 points between the first 62 and the second 70 images may be modeled by the second 82 deformation field as shown by vectors v(1,2) and v(2,2), respectively.

As illustrated in FIGS. 2 and 6, the first 78 and the second 82 deformation fields may be combined 88 to form/generate 52 the complex deformation field 54. Thus, the complex deformation field 52 contains information derived from both the first 78 and the second 82 deformation fields regarding the deformation caused/induced by the first 16 and the second 18 guide wires. For example, the vectors v(1,1) and v(1,2) may be summed to form vector v(1,c) which represents the deformation induced by both the first 16 and the second 18 guide wires on the first common point 84 between the first 62 and the second 70 images. Similarly, vectors v(2,1) and v(2,2) may be summed to form vector v(2,c) which represents the deformation induced by both the first 16 and the second 18 guide wires on the second common point 86 between the first 62 and the second images 70.

In embodiments, the first 78 and the second 82 deformation fields may be weighted 90. Weighting 90 the first 78 and the second 82 deformation fields may include assigning a weight for each of the first 78 and the second 82 deformation fields at at least one of the one or more common points 84, 86. For example, as shown in FIG. 6, vectors v(1,1) and v(1,2) may be assigned the weights w(1,1) and w(1,2), respectively. Similarly, vectors v(2,1) and v(2,2) may be assigned the weights w(2,1) and w(2,2), respectively. Accordingly, in such embodiments, v(1,c) may be the sum of w(1,1)v(1,1) and w(1,2)v(1,2), and v(2,c) may be the sum of w(2,1)v(2,1) and w(2,2)v(2,2). It is to be understood, however, that in embodiments which weight deformation fields, not all deformation fields which contribute to the generation of the complex deformation field 52 need be weighted.

Referring now to FIGS. 3 and 6, the assigned weight for both the first 78 and the second 82 deformation fields may be based at least in part on the location of the at least on point 84, 86 in relation to the first 16 and/or the second 18 landmarks/guide wires. In embodiments, the assigned weight for the first 78 and/or the second 82 deformation fields may be inversely proportional to a distance from at least one of the at least one point 84, 86 to the first 16 and/or the second 18 landmarks/guide wires. For example, d(1,1) may be shorter than d(1,2), thus the first guide wire 16 may induce more deformation on common point 84 than the second guide wire 18. Therefore, w(1,1) may be assigned a higher value than w(2,1). Similarly, d(2,2) may be shorter than d(2,1), thus, the second guide wire 18 may induce more deformation on common point 86 than the first guide wire 16. Therefore, w(2,2) may be given a higher value than w(2,1).

While the present disclosure demonstrates weighing the deformation fields 78 and 82 inversely proportional of the distance between the at least one point 84, 86 to the first 16 and/or the second 18 guide wires, it is to be understood that other weighting approaches may be applied. For example, in embodiments, the weights for each deformation field may be based on the physical characteristic (e.g., flexibility, compressibility, width, etc.) of the guide wires of which they model the deformation of.

Continuing on, generating 56 the composite image/frame 58 of the video feed 40 based at least in part the complex deformation field 54 may include registering the second image 70 to the first image 62 based at least in part on the complex deformation field 54. Registering the second image 70 to the first image 62 may be accomplished in a manner similar to those known in the art. As the complex deformation field 54 contains information regarding the deformation induced/caused by the guide wires 16 and 18, however, the complex deformation field 54 may be used during registration to attain a better alignment between the objects 12, 14, 16, 18 as shown in the first image 62 and the objects 12, 14, 16, 18 as shown in the second 70 image.

Figure 7:
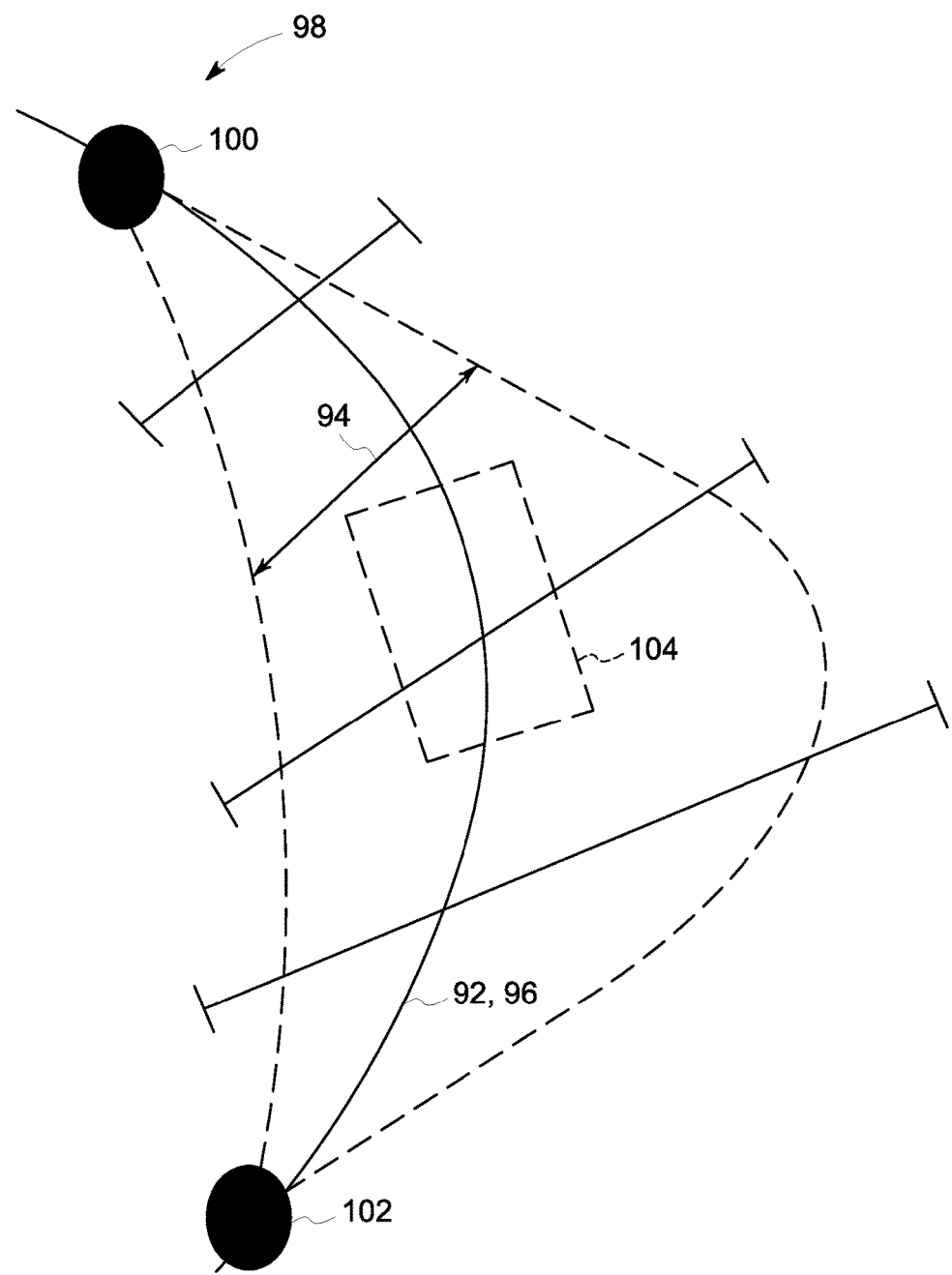
FIG. 7 is a diagram of a mathematical model for identifying the position of a guide wire in an image of the plurality of images acquired by the system of FIG. 1 in accordance with embodiments of the present invention.

Turning now to FIGS. 2 and 7, identifying 60, 68 the first 64, 66 and the second 72, 74 positions of the first 16 and second 18 landmarks/guide wires may be accomplished by using a mathematical model to estimate the actual position of the first 16 and the second 18 landmarks/guide wires in the first 62 and second 70 images. For example, as shown in FIG. 7, the controller 26 may use segmentation to determine one or more curves 92, from a range/family of possible curves 94, that most closely model the actual position of a guide wire 96 in an image 98. In embodiments, segmentation of the guide wire 96 may be accomplished in a manner similar to the methods disclosed and claimed by U.S. Pat. No. 7,734,328 B2 to Vaillant et. al., which is herein fully incorporated by reference.

Accordingly, in embodiments, identifying the position of a guide wire 96 may be assisted by one or more markers 100, 102 disposed on opposite sides of a stent 104. The markers 100 and 102 have a high contrast to noise ratio, thus making them readily detectable by the controller 26. The controller 26 may then generate the family of curves 94 such that each curve of the family passes through both markers 100 and 102. The controller 26 may then select one or more curves 92 from the family of possible curves 94 that most closely matches the true position of the guide wire 96. The one or more curves 92 may be selected via an exhaustive search of the family of curves 94.

Thus, as shown in FIG. 3-5, in embodiments, a first pair of markers 104, 106 may be supported by the first guide wire 16 such that markers 104 and 106 are disposed on opposite side of the first stent 12, and a second pair of markers 108, 110 may be supported by the second guide wire 18 such that markers 108 and 110 are disposed on opposite sides of the second stent 14. As will be appreciated, similar to the stenciling of the first positions 64, 66 of the first 16 and the second 18 guide wires in FIGS. 4 and 5 for the purpose of illustrating movement (disused above), markers 104 and 106 in FIG. 4 and markers 108 and 110 in FIG. 5 have also been stenciled in for the purpose of illustrating movement between the first 62 and second 70 images. In particular, in FIGS. 4 and 5, the solid black circles 104, 106, 108, and 110 represent the actual positions of the markers 104, 106, 108 and 110 in the second image 70, and the clear circles 104, 106, 108, and 110 represent the positions from which the markers 104, 106, 108, and 110 have moved from between the first 62 and the second images 70.

The markers 104, 106, 108, and 110 may be detected in the first 62 and the second 70 images by the controller which may then use geometric reasoning to group the markers 104, 106, 108, and 110 into the first 104, 106 and second 108, 110 pairs. For example, the controller may be configured to detect the relative motion of the markers 104, 106, 108, and 110 between the first 62 and second 70 images and then pair the markers 104, 106, 108, and 110 based on applying known geometric limitations to the detected relative motions of the markers 104, 106, 108, and 110.

As is to be appreciated, and as discussed above, the markers 104, 106, 108, 110 themselves may be one or more of the landmarks used to generate the complex deformation field 54. For example, in embodiments, the deformation caused by a guide wire 16 and/or 18 can be seen/calculated via the movement of a pair of markers 104, 106 and/or 108, 110, respectively. Thus, some embodiments may rely only on the identification of pairs of markers, as opposed to identifying the position of guide wires, to generate the first 78, second 82, and/or complex 54 deformation fields. It is to be understood, however, that as shown above, other embodiments may rely on identification of the guide wires 16, 18 and/or the markers 104, 106 and/or 108, 110 to generate first 78, second 82, and/or complex 54 deformation fields.

As is to be further appreciated, the system and methods disclosed herein may be adapted such that the generated frame 58 is three dimensional. For example, while the vectors shown herein depicting the first 78, the second 82, and the complex 54 deformation fields are two-dimensional, those skilled in the art will appreciate that such vectors can be extended to three-dimensional form, thereby producing a three-dimensional frame 58/video feed 40.

Additionally, while the embodiment shown in FIG. 6 depicts a complex deformation field 54 that is generated from two deformation fields 78 and 82, thus accounting for the deformation of two guide wires 16 and 18, it is to be understood that other embodiments may use three or more deformation fields to generate the complex deformation field 54. Thus, the complex deformation field 54 in such embodiments may account for the deformation caused by three or more guide wires. Therefore, it is also to be appreciated that the number of guide wires which can be accounted for by the complex deformation field 54 can be increased by increasing the number of deformation fields used to model the deformation induced/caused by each guide wire.

Accordingly, embodiments of the present invention provide many benefits over traditional imaging systems. For example, in some embodiments, the generation 52 of the complex deformation field 54 via generating/calculating one or more deformation fields 78, 82, where each of the deformation fields 78, 82 accounts for the deformation of one guide wire 16 or 18, allows such embodiments to simultaneously track the movements of two or more guide wires, which may or may not be marked by four or more markers 104, 106, 108, 110. This in turn allows for the simultaneous enhancement of multiple objects 12, 14, 16, 18 supported by the two or more guide wires 16, 18 within an imaged subject 20. Thus, some embodiments of the present invention allow for the tracking of two or more stents 12 and 14 in a patient 20 during an angioplasty procedure, which in turn reduces the level of risk to the patient 20 by reducing the amount of time required to place both stents 12 and 14. Additionally, some embodiments of the present invention also allow an operator performing an angioplasty to see better both stents 12 and 14 at once/simultaneously, thereby reducing the risk that either stent 12, 14 will be incorrectly deployed.

Further, by accounting for/modeling the deformation induced by two or more guide wires 16, 18, the complex deformation field 70 of some embodiments is elastic (e.g., non-rigid and/or no-affine) which in turns provides for smooth and/or continuous transformations (e.g. algebraic combinations of continuous transforms) during image registration.

As such, it is to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a method for enhancing the visualization of a plurality of objects within an imaged subject is provided. The method includes acquiring a plurality of images of the plurality of objects disposed in the imaged subject and supported by a plurality of guide wires; generating a complex deformation field based at least in part on a plurality of landmarks disposed in the plurality of images; and generating a composite image based at least in part on the complex deformation field. The complex deformation field models deformation induced on the plurality of objects by at least two or more guide wires of the plurality. In certain embodiments, generating the complex deformation field based at least in part on the plurality of landmarks includes: identifying, in a first image of the plurality, a first position of a first landmark of the plurality, and a first position of a second landmark of the plurality; identifying, in a second image of the plurality, a second position of the first landmark, and a second position of the second landmark; generating a first deformation field based at least in part on the first and the second positions of the first landmark; and generating a second deformation field based at least in part on the first and the second positions of the second landmark. In certain embodiments, generating the complex deformation field based at least in part on the plurality of landmarks further includes: weighting the first and the second deformation fields. In certain embodiments, weighting the first and the second deformation fields includes: assigning a weight for each of the first and the second deformation fields at at least one point common between the first and the second deformation fields. The assigned weight for both the first and the second deformation fields is based at least in part on the location of the at least one point in relation to the first and the second landmarks, respectively. In certain embodiments, the assigned weight for both the first and the second deformation fields is inversely proportional to a distance from the at least one point to at least one of the first and the second landmarks. In certain embodiments, at least one of the first and the second landmarks is a pair of markers. In certain embodiments at least one of the first and the second landmarks is a guide wire of the plurality. In certain embodiments, a pair of markers are disposed on the guide wire on opposite sides of at least one object of the plurality supported by the guide wire. In such embodiments, identifying, in the first image of the plurality, the first position of the first landmark of the plurality, and the first position of the second landmark of the plurality further includes modeling the guide wire as one or more curves that intercept the pair of markers. In certain embodiments, the one or more curves that model the guide wire are selected from a family of curves that intercept both markers of the pair of markers. In certain embodiments, the composite image is three dimensional.

In yet another embodiment, an imaging system for enhancing the visualization of two or more objects within an imaged subject is provided. The system includes a controller including at least one processor and a memory device. The memory device stores an imaging application which when loaded into the at least one processor adapts the controller to enhance, via a complex deformation field based at least in part on a plurality of landmarks disposed within a plurality of images acquired by the imaging system, the visibility of the two or more objects in a composite image. The complex deformation field models deformation induced on the two or more objects by two or more guide wires that support the two or more objects. In certain embodiments, the complex deformation field is further based at least in part on a first deformation field and a second deformation field. The first and the second deformation fields are generated by the controller and based at least in part on a first landmark of the plurality, and a second landmark of the plurality, respectively. In certain embodiments, the first and the second deformation fields are weighted. In certain embodiments, the first and the second deformation fields have one or more points in common, and the first and the second deformation fields are weighted at at least one point of the one or more points based at least in part on the location of the at least one point in relation to at least one of the first and the second landmarks. In certain embodiments, at least one of the first and the second deformation fields is weighted at the at least one point inversely proportional to a distance from the at least one point to at least one of the first and the second landmarks. In certain embodiments, at least one of the first and the second landmarks is a pair of markers. In certain embodiments, at least one of the first and the second landmarks is a guide wire, of the two or more guide wires, that supports an object of the two or more objects. In certain embodiments, a pair of markers are disposed on the guide wire on opposite sides of the object supported by the guide wire, and the controller is further adapted by the imaging application to model the guide wire as one or more curves that intercept the pair of markers. In certain embodiments, the composite image is three dimensional.

In yet another embodiment, a method for simultaneously enhancing the visualization two or more stents disposed within a patient is provided. The method includes: acquiring a first image and a second image; and applying a complex deformation field to at least one of the first and the second images to generate a frame of a video feed. Both images include the two or more stents, and each stent is supported by a guide wire that includes a pair of markers disposed on opposite sides of the stent. The complex deformation field is based at least in part on two or more weighted deformation fields. Each of the two or more weighted deformation fields is based at least in part on one or more of the pairs of markers of the guide wires supporting the two or more stents.

It is to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the imaging system 10 may include at least one processor 42, system memory 44 including random access memory (RAM) and read-only memory (ROM), an input/output controller, and one or more data storage structures. All of these latter elements may be in communication with the at least one processor 42 to facilitate the operation of the imaging system 10 as discussed above. Suitable computer program code may be provided for executing numerous functions, including those discussed above in connection with the imaging system 10 and methods disclosed herein.

The computer program code may also include program elements such as an operating system, a database management system and "device drivers" that allow the imaging system 10, to interface with computer peripheral devices (e.g., sensors, a video display, a keyboard, a computer mouse, etc.).

The at least one processor 42 of the imaging system 10 may include one or more conventional microprocessors and one or more supplementary co-processors such as math co-processors or the like. Elements in communication with each other need not be continually signaling or transmitting to each other. On the contrary, such elements may transmit to each other as necessary, may refrain from exchanging data at certain times, and may cause several steps to be performed to establish a communication link there-between.

The data storage structures such as memory discussed herein may include an appropriate combination of magnetic, optical and/or semiconductor memory, and may include, for example, RAM, ROM, flash drive, an optical disc such as a compact disc and/or a hard disk or drive. The data storage structures may store, for example, information required by the imaging system 10 and/or one or more programs (e.g., computer program code and/or a computer program product) adapted to direct the imaging system 10. The programs may be stored, for example, in a compressed, an uncompiled and/or an encrypted format, and may include computer program code. The instructions of the computer program code may be read into a main memory of a processor from a computer-readable medium. While execution of sequences of instructions in the program causes the processor to perform the process steps described herein, hard-wired circuitry may be used in place of, or in combination with, software instructions for implementation of the processes of the present invention. Thus, embodiments of the present invention are not limited to any specific combination of hardware and software.

The program may also be implemented in programmable hardware devices such as field programmable gate arrays, programmable array logic, programmable logic devices or the like. Programs may also be implemented in software for execution by various types of computer processors. A program of executable code may, for instance, includes one or more physical or logical blocks of computer instructions, which may, for instance, be organized as an object, procedure, process or function. Nevertheless, the executables of an identified program need not be physically located together, but may include separate instructions stored in different locations which, when joined logically together, form the program and achieve the stated purpose for the programs such as preserving privacy by executing the plurality of random operations. In an embodiment, an application of executable code may be a compilation of many instructions, and may even be distributed over several different code partitions or segments, among different programs, and across several devices.

The term "computer-readable medium" as used herein refers to any medium that provides or participates in providing instructions to at least one processor 42 of the imaging system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

Various forms of computer readable media may be involved in carrying one or more sequences of one or more instructions to at least one processor for execution. For example, the instructions may initially be borne on a magnetic disk of a remote computer (not shown). The remote computer can load the instructions into its dynamic memory and send the instructions over an Ethernet connection, cable line, or telephone line using a modem. A communications device local to a computing device (e.g., a server) can receive the data on the respective communications line and place the data on a system bus for at least one processor. The system bus carries the data to main memory, from which the at least one processor retrieves and executes the instructions. The instructions received by main memory may optionally be stored in memory either before or after execution by the at least one processor. In addition, instructions may be received via a communication port as electrical, electromagnetic or optical signals, which are exemplary forms of wireless communications or data streams that carry various types of information Further, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted based on 35 U.S.C. § 112(f), unless and until such claim limitations expressly use the phrase "means for" followed by a statement of function void of further structure.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted based on 35 U.S.C. § 112(f), unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A method for improving visibility of a plurality of objects within an imaged subject, the method comprising:
    operating a medical imaging system to:
        generate a plurality of images of a plurality of objects and landmarks supported by a plurality of guide wires disposed in an imaged subject, the plurality of landmarks comprising at least a first landmark and a second landmark;
        identify, in at least one image of the plurality of images, at least a first position of the first landmark and a first position of the second landmark;
        identify, in at least one other image of the plurality of images, at least a second position of the first landmark and a second position of the second landmark;
        generate at least a first deformation field based at least in part on the first and the second positions of the first landmark and a second deformation field based at least in part on the first and the second positions of the second landmark, the generated deformation fields modeling deformation induced on the plurality of objects by at least two guidewires of the plurality of guidewires; and
        generate a composite image based at least in part on the first and the second deformation fields resulting in improved visibility of the plurality of objects in the composite image relative to the visibility of said objects in the previously generated plurality of images; and
    displaying the composite image on a display screen with the improved visibility of the plurality of objects.

2. The method of claim 1, wherein generating the deformation fields further comprises weighting the first and the second deformation fields.

3. The method of claim 2, wherein weighting the first and the second deformation fields comprises assigning a weight for each of the first and the second deformation fields at least one common point between the first and the second deformation fields, the assigned weight for both the first and the second deformation fields based at least in part on the location of the at least one common point in relation to the first and the second landmarks, respectively.

4. The method of claim 3, wherein the assigned weight for both the first and the second deformation fields is inversely proportional to a distance from the at least one common point to at least one of the first and the second landmarks.

5. The method of claim 1, wherein at least one of the first and the second landmarks is a pair of markers.

6. The method of claim 1, wherein at least one of the first and the second landmarks is a guide wire of the plurality.

7. The method of claim 6, wherein a pair of markers are disposed on the guide wire on opposite sides of at least one object of the plurality supported by the guide wire, and
    identifying, in the first image of the plurality, the first position of the first landmark of the plurality, and the first position of the second landmark of the plurality further comprises:
    modeling the guide wire as one or more curves that intercept the pair of markers.

8. The method of claim 7, wherein the one or more curves that model the guide wire are selected from a family of curves that intercept both markers of the pair of markers.

9. The method of claim 1, wherein the composite image is three dimensional.

10. The method of claim 1, wherein the plurality of objects are two or more stents.

11. An imaging system for improving visibility of two or more objects within an imaged subject, the system comprising:
    a medical imaging device to generate a plurality of images of the subject including the two or more objects;
    a controller including at least one processor and a memory device that stores an imaging application, which when loaded into the at least one processor, enables the controller via a deformation field based at least in part on a plurality of landmarks disposed within the plurality of images acquired by the imaging device, to improve the visibility of the two or more objects in a composite image generated by the imaging system relative to the visibility of said objects in the previously generated plurality of images,
    wherein the deformation field models deformation induced on the two or more objects by at least two guide wires that support the two or more objects, and the deformation field is further based at least in part on a first deformation field and a second deformation field, the first and the second deformation fields generated by the controller and based at least in part on a first landmark and a second landmark of the plurality of landmarks, respectively; and
    a display screen to display the composite image generated by the controller with the improved visibility of the two or more objects.

12. The system of claim 11, wherein the first and the second deformation fields are weighted.

13. The system of claim 11, wherein the first and the second deformation fields have one or more points in common, and the first and the second deformation fields are weighted at least one point of the one or more points based at least in part on the location of the at least one point in relation to at least one of the first and the second landmarks.

14. The system of claim 13, wherein at least one of the first and the second deformation fields is weighted at the at least one point inversely proportional to a distance from the at least one point to at least one of the first and the second landmarks.

15. The system of claim 11, wherein at least one of the first and the second landmarks is a pair of markers.

16. The system of claim 11, wherein at least one of the first and the second landmarks is a guide wire, of the two or more guide wires, that supports an object of the two or more objects.

17. The system of claim 11, wherein a pair of markers are disposed on the guide wire on opposite sides of the object supported by the guide wire, and
    the controller is further configured by the imaging application to model the guide wire as one or more curves that intercept the pair of markers.

18. The system of claim 11, wherein the composite image is three dimensional.

* * * * *